United States Patent [19]

Sunagawa et al.

[11] Patent Number: 4,888,344
[45] Date of Patent: Dec. 19, 1989

[54] CARBAPENEM COMPOUND IN CRYSTALLINE FORM, AND ITS PRODUCTION AND USE

[75] Inventors: Makoto Sunagawa, Itami; Yutaka Isobe, Nishinomiya; Yutaka Takeuchi, Toyonaka; Haruki Matsumura, Nara; Yukio Ozaki, Takatsuki; Tetsuo Noguchi, Suita, all of Japan

[73] Assignee: Sumitomo Pharmaceuticals Company, Limited, Osaka, Japan

[21] Appl. No.: 79,470

[22] Filed: Jul. 30, 1987

[30] Foreign Application Priority Data

Jul. 30, 1986 [JP] Japan .................. 61-179321
Jun. 26, 1987 [JP] Japan .................. 62-157769

[51] Int. Cl.$^4$ .................. C07D 487/04; A61K 31/40
[52] U.S. Cl. .................. 514/210; 540/350
[58] Field of Search .................. 540/350; 514/210

[56] References Cited

U.S. PATENT DOCUMENTS 4,748,238  3/1988  Shih .................. 540/350

FOREIGN PATENT DOCUMENTS 006639   1/1980   European Pat. Off. .......... 540/350
126587  11/1984   European Pat. Off. .......... 540/350
0162242  4/1985   European Pat. Off. .
0181571 10/1985   European Pat. Off. .
0188816  7/1986   European Pat. Off. .

3619200 12/1986 Fed. Rep. of Germany .

OTHER PUBLICATIONS

Jeffrey et al., "Homogeneous, Palladium(o)—Catalyzed Exchange Deprotection . . . ", J. Org. Chem., 1982, pp. 47, 587–590.
Girijavallabhan et al., "Synthesis of Optically Active Penems", Tetrahedron Letters, 22, No. 36, pp. 3485–3488 (1981).
Minami et al., "Palladium-Catalyzed Reaction . . . ", Tetrahedron Letters, 26, No. 20, pp. 2449–2452 (1985).

Primary Examiner—Robert Gerstl
Attorney, Agent, or Firm—Birch, Stewart, Kolasch & Birch

[57] ABSTRACT

(4R,5S,6S 8R,2'S,4'S)-3-[4-(2-Dimethylaminocarbonyl)pyrrolidinylthio]-4-methyl-6-(1-hydroxyethyl)-1-azabicyclo[3.2.0]hept-2-en-7-one-2-carboxylic acid of the formula:

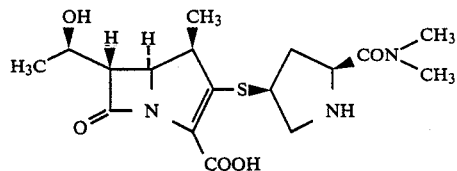

in a crystalline form, which is useful as an antibiotic agent.

4 Claims, No Drawings

CARBAPENEM COMPOUND IN CRYSTALLINE FORM, AND ITS PRODUCTION AND USE

The present invention relates to a carbapenem compound in a crystalline form, and its production and use.

The carbapenem compound in this invention is (4R,5S,6S,8R,2'S,4'S)-3-[4-(2-dimethylaminocarbonyl)-pyrrolidinylthio]-4-methyl-6-(1-hydroxyethyl)-1-azabicyclo[3.2.0]hept-2-en-7-one-2-carboxylic acid (hereinafter referred to as "Compound A") of the formula:

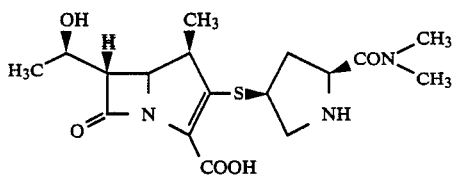

which has a broad antimicrobial spectrum and a strong antimicrobial activity and is useful as an antibiotic agent.

Compound A in a non-crystalline form, i.e. as an amorphous powder obtained by lyophilization, and its use as an antibiotic agent are reported in EP 126587A. However, Compound A in such non-crystalline form is not sufficiently stable and decomposes with decrease of its antibiotic potency during the storage over a long period of time.

As a result of the extensive study, it has now been succeeded in obtaining Compound A in a crystalline form with a high purity. Further, it has been found that Compound A in such crystalline form is much more stable than that in a non-crystalline form and suitable for storage. Besides, Compound A can be readily purified through such crystalline form.

Crystalline Compound A according to the invention can be administered parenterally, i.e. by injection, in view of its high purity. For administration by injection, crystalline Compound A may be incorporated with any nontoxic carbonate to make a readily soluble preparation. On the practical administration, this preparation may be dissolved in a physiologically acceptable aqueous medium such as distilled water or physiological saline to make an injectionable composition. Advantageously, crystalline Compound A is quite stable even in the state of a mixture with a non-toxic carbonate, and such mixture itself is suitable for storage over a long period of time.

For preparation of crystalline Compound A, an aqueous solution of a crude product of Compound A is cooled and/or diluted with a water-miscible organic solvent to make Compound A supersaturated. Alternatively, non-crystalline Compound A may be dissolved in an aqueous medium such as water or its mixture with a water-miscible organic solvent, followed by cooling and/or dilution with a water-miscible organic solvent to make Compound A supersaturated.

Prior to said cooling and/or dilution, the aqueous solution containing Compound A may be appropriately concentrated, if necessary. Such concentration of the Compound A-containing solution as an optional step may be carried out, for instance, by heating under atmospheric or reduced pressure to evaporate water. Alternatively, the concentration may be achieved by adaptation of any membrane separation procedure such as reverse osmosis to eliminate water. In general, membrane separation is favorable, because concentration can be attained at a low temperature without decomposition of Compound A. Examples of the membrane for reverse osmosis as usable are a polyacrylonitrile membrane, a polyvinyl alcohol membrane, a polyamide membrane, a cellulose acetate membrane, etc.

The Compound A content in the aqueous solution at the initiation of cooling and/or dilution is not limitative but usually from about 0.5 to 20% by weight on the basis of the weight of water in said aqueous solution. Such aqueous solution, i.e. a saturated or nearly saturated solution of Compound A, is subjected to cooling by temperature lowering and/or dilution by incorporation of a water-miscible organic solvent therein until a supersaturation state is obtained. The starting saturated or nearly saturated solution and the resultant supersaturated solution may be at any appropriate temperatures and are usually and respectively from about 20° to 50° C. and from about 0° to 20° C. Temperature lowering may be effected at a relatively slow rate, preferably under stirring.

Crystallization of Compound A from the supersaturated solution thus obtained can take place automatically, for instance, at the surface of a reactor or an agitator therein. Alternatively, it may be achieved by incorporation of seed crystals therein.

Recovery of the crystallized Compound A may be accomplished by application of a separation procedure as conventionally adapted for a solid/liquid mixture. For instance, the mixture is subjected to filtration, filtration under pressure, filtration with vacuum suction, centrifugation, decantation or the like to collect the crystals. The collected crystals are then dried usually at room temperature or slightly higher temperature (e.g. about 15° to 50° C.), preferably at a temperature from about 20° to 30° C., until the weight is made almost constant. For acceleration of drying, the operation may be carried out under reduced pressure.

As the water-miscible organic solvent used in the above procedure, there may be exemplified lower alkanols (e.g. methanol, ethanol, propanol, isopropanol), ketones (e.g. acetone, methylethylketone), esters (e.g. methyl acetate, ethyl acetate), aliphatic hydrocarbons (e.g. hexane, heptane), aromatic hydrocarbons (e.g. toluene, xylene), halogenated hydrocarbons (e.g. dichloromethane, dichloroethane), ethers (e.g. tetrahydrofuran, dioxane), amides (e.g. dimethylformamide, dimethylacetamide), nitriles (e.g. acetonitrile, propionitrile), etc. Preferred are ethanol, isopropanol, acetone, tetrahydrofuran, dioxane, acetonitrile, etc. These may be used alone or in combination.

The crystalline Compound A as obtained forms usually a trihydrate and contains water in an amount of about 12% by weight. Any crystalline product having a lower water content can be obtained by drying. Thus, crystalline Compound A of this invention is not necessarily limited to said trihydrate.

Compared with conventional non-crystalline Compound A, crystalline Compound A of this invention is advantageous in being highly stable and stored without any material change over a long period of time. When, for instance, kept in a sealed bottle at a temperature of 50° C., crystalline Compound A (trihydrate) of the invention did not produce any decomposition even after 6 months, whereas conventional non-crystalline Compound A showed the remaining rate of only 51.8% and 32.6% respectively after 7 days and 11 days.

Crystalline Compound A may be administered as such or in any per se conventional preparation form, but its administration through a parenteral route is generally favorable because of the rapid and assured exertion of the antimicrobial activity. Quite advantageously, crystalline Compound A is stable even in the presence of carbonates, and therefore it may be incorporated with a non-toxic carbonate to formulate a readily water-soluble powdery preparation. On the use, this preparation is dissolved into an aqueous medium and then administered as an injection. As the non-toxic carbonate, there may be used, for instance, alkali metal bicarbonates (e.g. sodium bicarbonate, potassium bicarbonate), etc. The equivalent proportion of crystalline Compound A and the non-toxic carbonate may be usually about 1: 0.5–3.5, preferably about 1: 1–2. In case of the non-toxic carbonate being a monoacidic base such as sodium bicarbonate, for instance, it may be used in an amount of about 1 to 2 mol to 1 mol of crystalline Compound A. Formulation may be carried out by a per se conventional mixing procedure. When desired, any per se conventional additive such as a local anesthetic agent (e.g. lidocaine hydrochloride, mepivacaine hydrochloride) may be additionally incorporated therein. The thus formulated composition is usually filled into ampoules or vials aseptically. If necessary, sealing may be effected in vacuo; the degree of vacuum in this case is usually not more than about $4 \times 10^4$ Pa.

Compound A in a non-crystalline form can be produced, for instance, from the corresponding protected carbapenem compound of the formula:

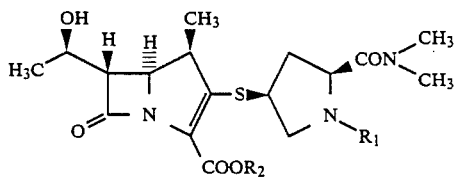

wherein $R_1$ is a protective group for amino and $R_2$ is a protective group for carboxyl (hereinafter referred to as "Compound B") by eliminating the protective groups $R_1$ and $R_2$ stepwise in an optional order or simultaneously in a single step. In general, simultaneous elimination is favored.

As the protective group for amino represented by $R_1$, there may be exemplified, for instance, a benzyloxycarbonyl group optionally substituted with nitro (e.g. benzyloxycarbonyl, p-nitrobenzyloxycarbonyl, o-nitrobenzyloxycarbonyl), a $C_3$–$C_7$ alkenyloxycarbonyl group optionally substituted with halogen such as chlorine or bromine (e.g. allyloxycarbonyl, 2-chloroallyloxycarbonyl), a tri($C_1$–$C_4$)alkylsilyl group (e.g. trimethylsilyl, triethylsilyl, t-butyldimethylsilyl group), etc. Examples of the protective group for hydroxyl represented by $R_2$ include a benzyl group optionally substituted with nitro (e.g. benzyl, p-nitrobenzyl, o-nitrobenzyl), a $C_3$–$C_7$ alkenyl group optionally substituted with halogen such as chlorine or bromine (e.g. allyl, 2-chloroallyl), an ethyl group substituted with tri($C_1$–$C_4$)alkylsilyl at the 2-position (e.g. 2-trimethylsilylethyl), a tri($C_1$–$C_4$)alkylsilyl group (e.g. trimethylsilyl, triethylsilyl, t-butyldimethylsilyl), etc.

Elimination of said protective groups may be accomplished by a per se conventional procedure. When, for instance, $R_1$ is a tri($C_1$–$C_H$)alkylsilyl group or $R_2$ is a tri($C_1$–$C_4$)alkylsilyl group or an ethyl group substituted with tri($C_1$–$C_4$)alkylsilyl, elimination can be made by treatment with a salt of hydrofluoric acid capable of producing fluoride anion such as an alkali metal fluoride (e.g. sodium fluoride, potassium fluoride) in the presence of a crown ether, treatment with a fluoride of an organic quarternary base such as tetra($C_1$–$C_4$)alkylammonium fluoride (e.g. tetraethylammonium fluoride, tetra-n-butylammonium fluoride) or treatment with an acidic buffer comprising an organic or inorganic acid (e.e. phosphoric acid, acetic acid, citric acid). When $R_1$ is a benzyloxycarbonyl group optionally substituted with nitro or $R_2$ is a benzyl group optionally substituted with nitro, elimination is performed by catalytic hydrogenation in the presence of a catalyst (e.g. palladium, platinum). When $R_1$ is an o-nitrobenzyloxycarbonyl group or $R_2$ is an o-nitrobenzyl group, elimination is also effected by photo-chemical reaction in addition to the catalytic hydrogenation. When $R_1$ is a $C_3$–$C_7$ alkenyloxycarbonyl group optionally substituted with halogen or $R_2$ is a $C_3$–$C_7$ alkenyl group optionally substituted with halogen, elimination is achieved by treatment with a catalytic amount of an organic solvent-soluble palladium complex having a phosphine legand (e.g. tetrakistriphenylphosphine palladium) in the presence of an alkenyl group-acceptor.

In this invention, it is preferred that $R_1$ is a benzyloxycarbonyl group optionally substituted with nitro and $R_2$ is a benzyl group optionally substituted with nitro, particularly $R_1$ is a p-nitrobenzyloxycarbonyl group and $R_2$ is a p-nitrobenzyl group. It is also preferred that $R_1$ is a $C_3$–$C_7$ alkenyloxycarbonyl group and $R_2$ is a $C_3$–$C_7$ alkenyl group, especially $R_1$ is an allyloxycarbonyl group and $R_2$ is an allyl group. In these cases, simultaneous elimination of two protective groups can be readily accomplished by the procedures as explained below.

(a) When $R_1$ is a benzyloxycarbonyl group optionally substituted with nitro (e.g. p-nitrobenzyloxycarbonyl) and $R_2$ is a benzyl group optionally substituted with nitro (e.g. p-nitrobenzyl), Compound B is subjected to reduction, particularly catalytic hydrogenation in the presence of a catalyst. As the catalyst, the use of a palladium-containing catalyst (e.g. palladium-carbon, palladium hydroxide-carbon, palladium-calcium carbonate, palladium-barium sulfate, palladium-aluminum)or a platinum-containing catalyst (e.g. platinum oxide, platinum-carbon) is favorable. Among them, the use of palladium-carbon, palladium hydroxide-carbon, platinum oxide or the like is particularly favored. The catalytic hydrogenation is usually effected in an inert solvent at a temperature of about 0° to 100° C., preferably of about 0° to 50° C. in the presence of hydrogen. The inert solvent may be chosen from lower alkanols (e.g. methanol, ethanol), ethers (e.g. tetrahydrofuran, dioxane), acetic acid, their mixtures with water or buffers comprising phosphoric acid or morpholinopropanesulfonic acid, etc., among which a mixture of tetrahydrofuran and water or morpholinopropanesulfonate buffer is favorable. The pressure of hydrogen may be atmospheric or elevated one, usually from atmospheric pressure to 100 kg/cm².

After completion of the catalytic hydrogenation, the catalyst is removed by filtration from the reaction mixture containing Compound A. The filtrate is concentrated and optionally desalted by treatment with an adsorptive resin (e.g. resinous gel "HP-20P" manufactured by Mitsubishi Chemical), followed by lyophilization to obtain Compound A in a non-crystalline form.

When the catalytic hydrogenation is carried out in a water-containing organic solvent, the filtrate obtained by filtration of the reaction mixture for removal of the catalyst may be subjected to distillation for evaporation of the organic solvent. In such case, Compound A can be crystallized out directly from the resultant aqueous concentrate. Thus, crystalline Compound A is obtainable without separation and isolation of non-crystalline Compound A, for instance, by column chromatography or lyophilization. Compared with said procedure wherein non-crystalline Compound A is once recovered, this procedure is favorable for efficient production of Compound A in a crystalline form, because non-crystalline Compound A has a problem in stability as stated above.

(b) When $R_1$ is a $C_3$–$C_7$ alkenyloxycarbonyl group (e.g. allyloxycarbonyl) and $R_2$ is a $C_3$–$C_7$ alkenyl group (e.g. allyl), Compound B is treated with a catalytic amount of tetrakistriphenylphosphine palladium in the presence of an alkenyl group acceptor. As the alkenyl group acceptor, there may be exemplified sterically hindered amines (e.g. t-butylamine), tri($C_1$–$C_4$)alkylamines (e.g. triethylamine, diisopropylethylamine), cyclic amines (e.g. pyrrolidine, piperidine, morpholine, thiomorpholine), aromatic amines (e.g. aniline, N-methylaniline), aliphatic or alicyclic beta-dicarbonyl compounds (e.g. acetylacetone, ethyl acetacetate, 1, 3-cyclohexanedione, dimedone), $C_2$–$C_9$ alkane-carboxylic acids (e.g. acetic acid, propionic acid, 2-ethylhexanoic acid) and their alkali metal salts (e.g. sodium salt, potassium salt), etc. These may be used alone or in combination. Among them, preferred are alicyclic beta-dicarbonyl compounds such as 1, 3-cyclohexanedione and dimedone and aromatic amines such as aniline and N-methylaniline. The alkenyl group acceptor is employed usually in an amount of from about 1.5 to 10 equivalents to Compound B. The amount of tetrakistriphenlphosphine palladium may be a catalytic one and usually from about 2 to 20 mol % on the basis of Compound B. The treatment is normally effected in an inert solvent at room temperature or somewhat lower or higher temperatures such as about 0° to 70° C. (especially about 10° to 50° C.), optionally in an inert gas (e.g. nitrogen, argon). Examples of the inert solvent are ethers (e.g. diethyl ether, tetrahydrofuran, dioxane), aromatic hydrocarbons (e.g. benzene, toluene), acetic esters (e.g. ethyl acetate, isopropyl acetate), halogenated hydrocarbons (e.g. methylene chloride, chloroform, 1, 2-dichloroethane), acetonitrile, etc., among which preferred are acetic esters, tetrahydrofuran, methylene chloride, etc. Their mixtures are also usable.

After completion of the reaction, the reaction mixture may be combined with an appropriate amount of water and separated into the aqueous phase and the organic solvent phase. The aqueous phase is washed with an organic solvent repeatedly so as to eliminate impurities therein and then subjected to crystallization of Compound A. By this procedure, crystalline Compound A is obtainable without separation and purification of non-crystalline Compound A.

In comparison between the above two procedures, Procedure (b) is generally more advantageous than Procedure a) in using the the transition metal for the catalyst and the solvent in lesser amounts.

Compound B itself is generically known and can be produced by per se known processes, for instance, as disclosed in EP-126587A and EP-188816A. A typical example is shown in the following scheme:

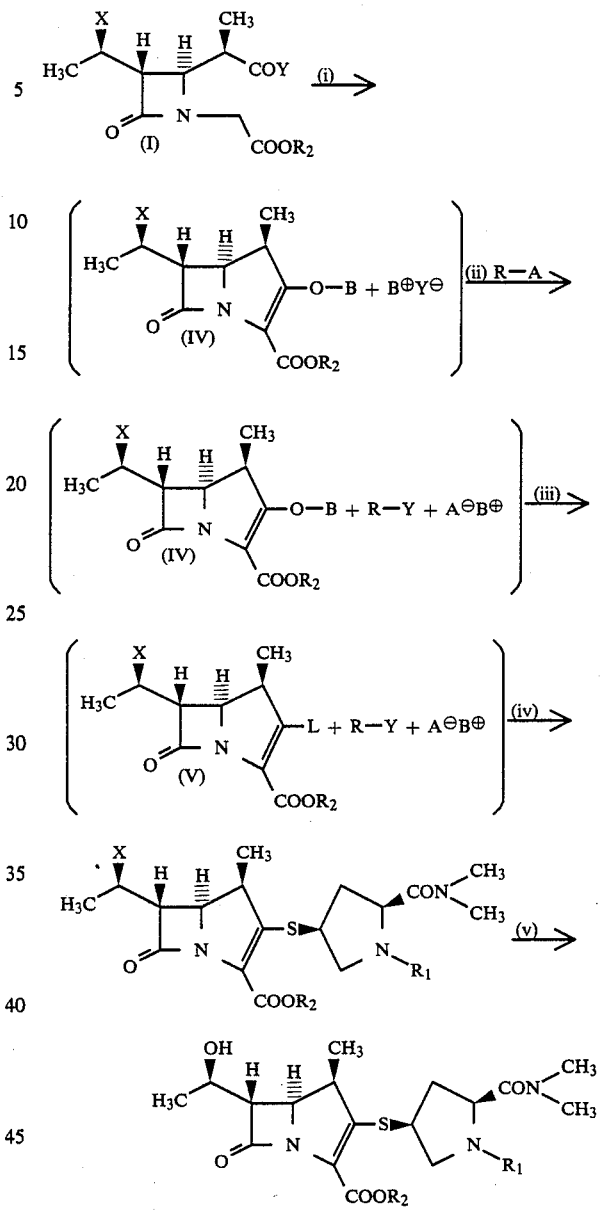

wherein $R_1$ and $R_2$ are each as defined above, X is a protected hydroxyl group (i.e. a hydroxyl group protected with a protective group for hydroxyl), COY is the residue of an active carboxylic ester or anhydride, a protected thiolcarboxyl group, a substituted aryloxycarbonyl group or a heteroaryloxycarbonyl group, B is an alkali metal atom, R-A is an alkylating or acylating agent and L is the residue of an active ester for hydroxyl.

Explaining the conversions in the above scheme, the beta-lactam compound (I) is treated with a base in an inert solvent to give the compound (IV) (step (i)). The compound (IV) is treated with an alkylating agent (e.g. iodomethane, iodopropane, allyl bromide, benzyl bromide, methyl p-toluenesulfonate) or an acylating agent (e.g. p-toluenesulfonyl chloride, methanesulfonyl chloride) to capture the group Y in the former with the latter (step (ii)), followed by treatment with an active esterifying agent for hydroxyl to give the compound (V) (step (iii)). Then, the compound (V) is reacted with a mercaptan of the formula:

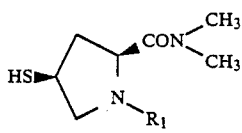

wherein $R_1$ is as defined above, if necessary, in the presence of a base to give the compound (III) (step (iv)). The compound (III) is then subjected to elimination of the protective group for hydroxyl to give Compound B (step (v)). In the above conversions, the product at each step is not necessarily required to be separated from the reaction mixture; namely, the reaction mixture in any step may be as such subjected to the reaction in the subsequent step.

In the starting beta-lactam compound (I), the protective group for hydroxyl represented by X is not limitative and may be any conventional one chosen from a $C_1$–$C_4$ alkoxycarbonyl group optionally substituted with halogen such as chlorine, bromine or iodine (e.g. t-butoxycarbonyl, 2-iodoethyloxycarbonyl, 2, 2, 2-trichloroethyloxycarbonyl), a $C_3$–$C_7$ alkenyloxycarbonyl group optionally substituted with halogen (e.g. allyloxycarbonyl, 2-chloroallyloxycarbonyl), a benzyloxycarbonyl group optionally substituted with nitro or methoxy (e.g. benzyloxycarbonyl, p-nitrobenzyloxycarbonyl, o-nitrobenzyloxycarbonyl, p-methoxybenzyloxycarbonyl), a tri($C_1$–$C_4$)alkylsilyl group (e.g. trimethylsilyl, triethylsilyl, t-butyldimethylsilyl), a substituted methyl group (e.g. methoxymethyl, 2-methoxyethoxymethyl, methylthiomethyl), a tetrahydropyranyl group, etc.

When the group COY in the compound (I) represents the residue of an active carboxylic ester or anhydride, the symbol Y may be a halogen atom (e.g. chlorine, bromine, iodine), a $C_1$–$C_5$ alkoxycarbonyl group (e.g. ethoxycarbonyloxy, isopropyloxycarbonyl, sec-butoxycarbonyl), a $C_1$–$C_4$ alkanesulfonyloxy group (e.g. methanesulfonyloxy), an arylsulfonyloxy group (e.g. p-toluenesulfonyloxy), a di($C_1$–$C_4$)alkylphosphoryloxy group (e.g. dimethylphosphoryloxy, diethylphosphoryloxy), a diarylphosphoryloxy group (e.g. diphenylphosphoryloxy), a cyclic imidoxy group (e.g. N-succinimidoxy, N-phthalimidoxy), a heteroaryl group (e.g. imidazolyl, triazolyl), a heterocycloalkyl group (e.g. 3-(2-thioxo)thiazolydinyl) or the like. When the group COY represents a protected thiolcarboxyl group, the protective group therein may be a $C_1$–$C_4$ alkyl group optionally substituted with halogen (e.g. methyl, ethyl, isopropyl, t-butyl, 2-iodoethyl, 2, 2, 2-trichloroethyl), a $C_3$–$C_7$ alkenyl group optionally substituted with halogen or lower alkyl (e.g. allyl, 2-methylallyl, 2-chloroallyl), a phenyl group optionally substituted with halogen, nitro or methoxy (e.g. phenyl, p-chlorophenyl, 2, 4, 6-trichlorophenyl, p-nitrophenyl, o-nitrophenyl, p-methoxyphenyl), a heteroaryl group (e.g. 2-pyridyl, 3-pyridyl, 4-pyridyl, 2-pyrimidyl, 2-(4, 6-dimethyl)pyrimidyl) or the like.

With respect to the step (i), examples of the base are an alkali metal hydride (e.g. sodium hydride, potassium hydride), sodium methylsulfinylmethide, metal salts of amines (e.g. lithium diisopropylamide, lithium bis(trimethylsilyl)amide, sodium amide), etc., and examples of the inert solvent are ethers (e.g. diethyl ether, tetrahydrofuran, dioxane), aromatic hydrocarbons (e.g. benzene, toluene), acetonitrile, dimethylformamide, dimethylsulfoxide, etc. These may be used solely or in combination.

The active esterifying agent for hydroxyl to be used in the step (iii) may be chosen from diphenylphosphoryl chloride, p-toluenesulfonyl chloride, methanesulfonyl chloride, etc.

The base usable in the step (iv) may be chosen from those as exemplified with respect to the step (i) and also from organic bases such as triethylamine, diisopropylethylamine, 4-dimethylaminopyridine, 1, 8-diazabicyclo-[5.4.0]undec-7-ene (DBU), 1, 5-diazabicyclo[4.3.0]non-5-ene (DBN) and 1, 4-azabicyclo[2.2.2]octane (DABCO). When desired, an inert solvent such as acetonitrile, dimethylformamide and dimethylsulfoixde may be used additionally in order to accelerate the reaction.

Throughout the steps (i) to (iv), the reagents including the mercapto compound (II) are to be used in such amounts as to assure the smooth proceeding of the reaction in each step. The base in the step (i) is normally used in an amount of 2 to 4 equivalents, while the other reagents are generally employed in amounts of 1 to 1.5 equivalents. Further, the reaction in each step is generally achieved at a temperature of about $-78°$ to $60°$ C., preferably of about $-40°$ to $10°$ C.

Removal of the protective group for hydroxyl in the step (v) may be achieved by an appropriate procedure depending on the kind of such protective group; typical examples of the conventional procedure are those as adapted for removal of the protective group $R_1$ or of the protective group $R_2$ and also hydrolysis, catalytic reduction, treatment with an acid or a base, reduction, etc. It is still possible to effect removal of the protective group for hydroxyl simultaneously with removal of the protective group $R_1$ and/or the protective group $R_2$. Practical and presently preferred embodiments of the invention are illustratively shown in the following Examples. However, the scope of this invention is not limited thereto. Further, in Reference Examples as hereinafter shown, the abbreviations have the following meanings:

Ph: phenyl group
Me: methyl group
AOC: allyloxycarbonyl group
TBDMS: t-butyldimethylsilyl group
t-Bu: t-butyl group

EXAMPLE 1

A lyophilized product of non-crystalline (4R,5S,6S,8R,2'S,4'S)-3-[4-(2-dimethylaminocarbonyl)pyrrolidinylthio]-4-methyl-6-(1-hydroxyethyl)-1-azabicyclo[3.2.0]-hept-2-en-7-one-2-carboxylic acid (Compound A) (5.0 g) was dissolved in water (50 ml) at 30° C. and cooled in a water bath, whereupon precipitation of a small amount of crystals was observed. Acetone (250 ml) was added thereto, and the resultant mixture was stirred for 1 hour. The precipitated crystals were collected by filtration, washed with acetone (90 ml) and dried at room temperature under reduced pressure for 2 hours to give 4.7 g of crystalline Compound A (trihydrate).

Elementary analysis for $C_{17}H_{25}N_3O_5S \cdot 3H_2O$:
Calcd.: C, 46.67%; H, 7.14%; N, 9.60%; S, 7.33%.
Found: C, 46.32%; H, 7.41%; N, 9.71%; S, 7.24%.

Crystalline Compound A (trihydrate) as obtained above gave the following powdery X-ray pattern in which $I/I_1$ indicates the relative intensity when the maximum diffraction intensity is taken as 100:

| (Spacing in lattice) | $I/I_l$ (Relative intensity) |
|---|---|
| 1.81 | 5 |
| 1.95 | 4 |
| 2.04 | 6 |
| 2.15 | 7 |
| 2.45 | 8 |
| 2.29 | 12 |
| 2.37 | 4 |
| 2.39 | 4 |
| 2.53 | 10 |
| 2.58 | 17 |
| 2.66 | 7 |
| 2.80 | 15 |
| 2.86 | 7 |
| 2.94 | 16 |
| 3.01 | 9 |
| 3.07 | 9 |
| 3.14 | 9 |
| 3.30 | 16 |
| 3.35 | 6 |
| 3.44 | 8 |
| 3.52 | 16 |
| 3.79 | 31 |
| 3.88 | 14 |
| 3.96 | 20 |
| 4.04 | 28 |
| 4.34 | 12 |
| 4.41 | 10 |
| 4.57 | 12 |
| 4.64 | 34 |
| 4.80 | 15 |
| 5.15 | 2 |
| 5.25 | 71 |
| 5.35 | 39 |
| 6.71 | 2 |
| 6.89 | 100 |
| 7.88 | 30 |

EXAMPLE 2

Crystalline Compound A (trihydrate) (568 mg) as obtained in Example 1 and sodium carbonate (103 mg) were charged in a vial, which was then sealed to give an injectionable preparation to be dissolved on the use.

EXAMPLE 3

(4R,5S,6S,8R,2'S,4'S)-p-Nitrobenzyl-3-[4-(1-p-nitrobenzyloxycarbonyl-2-dimethylaminocarbonyl)-pyrrolidinylthio]-4-methyl-6-(1-hydroxyethyl)-1-azabicyclo[3.2.0]-hept-2-en-7-one-2-carboxylate (content, 78%; 3.0 g) was dissolved in tetrahydrofuran (177 g), water (240 g) and 10% palladium-carbon (6.0 g) were added thereto, and hydrogen was introduced therein at room temperature under a hydrogen pressure of 5 kg/cm²G for 5 hours. After removal of the catalyst by filtration, the filtrate was washed with water, followed by distillation under reduced pressure to remove tetrahydrofuran. The residue was washed with dichloromethane, and the aqueous layer was again subjected to distillation under reduced pressure to remove the organic solvent, whereby an aqueous solution of the crude product (472 g) was obtained. A portion (230 g) of the aqueous solution was concentrated by the use of a plain membrane type reverse osmosis condensing apparatus under a pressure of 50 kg/cm²G. The resulting condensate (7.7 g) was cooled to 5° C., and tetrahydrofuran (7.7 ml) was added thereto, followed by stirring for 1 hour. Tetrahydrofuran (30.8 ml) was added thereto, followed by stirring for 1 hour. The precipitated crystals were collected by filtration, washed with tetrahydrofuran (15 ml) and dried at room temperature under reduced pressure for 2 hours to give 390 mg of crystalline Compound A (trihydrate).

EXAMPLE 4

In the same manner as in Example 1 but using tetrahydrofuran in place of acetone, there was obtained 152 mg of crystalline Compound A (trihydrate) from 200 mg of the lyophilized product of non-crystalline Compound A.

EXAMPLE 5

In the same manner as in Example 1 but using isopropanol in place of acetone, there was obtained 140 mg of crystalline Compound A (trihydrate) from 200 mg of the lyophilized product of non-crystalline Compound A.

EXAMPLE 6

(4R,5S,6S,8R,2'S,4'S)-Allyl-3-[4-(1-allyloxy-carbonyloxy-2-dimethylaminocarbonyl)pyrrolidinylthio]-4-methyl-6-(1-hydroxyethyl)-1-azabicyclo[3.2.0]hept-2-en-7-one-2-carboxylate (content, 67%; 1.033 g) was dissolved in ethyl acetate (20.7 ml), dimedone (0.85 g) was added thereto, and argon was introduced therein for 5 minutes, followed by heating at 30° C. A solution of tetrakistriphenylphosphine palladium (155 mg) in methylene chloride (5 ml) was dropwise added thereto at 30° C., and the reaction mixture was stirred at the same temperature for 3 hours under nitrogen stream. Water (10.3 ml) was added thereto while stirring. The aqueous layer was separated, washed with ethyl acetate (10 ml×2) and added portinwise to ice-cooled tetrahydrofuran (20 ml), followed by stirring while ice-cooling for 30 minutes. To the resulting mixture, about 1 mg of crystals of Compound A (trihydrate) was added, followed by portionwise addition of tetrahydrofuran (30 ml). Stirring was continued for 2 hours under ice-cooling. The precipitated crystals were collected by filtration, washed with tetrahydrofuran (10 ml) and dried at room temperature under reduced pressure for 5 hours to give 323 mg of crystalline Compound A (trihydrate).

EXAMPLE 7

A solution of aniline (149 mg) in isopropyl acetate (4 ml) was refluxed for 30 minutes, followed by cooling to 30° C. (4R,5S,6S,8R,2'S,4'S)-Allyl-3-[4-(1-allyloxycarbonyl-2-dimethylaminocarbonyl)pyrrolidinylthio]-4-methyl-6-(1-hydroxyethyl)-1-azabicyclo[3.2.0]hept-2-en-7-on-2-carboxylate (102 mg) and tetrakistriphenylphosphine palladium (46 mg) were added thereto at 30° C., and the resultant mixture was stirred at 30° C. for 3 hours under nitrogen stream. The reaction mixture was post-treated in the same manner as in Example 6 to give crystalline (4R,5S,6S,8R,2'S,4'S)-3-[4-(2-dimethylaminocarbonyl)pyrrolidinylthio]-4-methyl-6-(1-hydroxyethyl)-1-azabicyclo[3.2.0]-hept-2-en-7-on-2-carboxylic acid (trihydrate).

EXAMPLE 8

In the same manner as in Example 7 but using N-methylaniline (129 mg) instead of aniline, there was produced crystalline (4R,5S,6S,8R,2'S,4'S)-3-[4-(2-dimethylaminocarbonyl)pyrrolidinylthio]-4-methyl-6-(1-hydroxyethyl)-1-azabicyclo[3.2.0]hept-2-en-7-on-2-carboxylic acid (trihydrate).

INTERMEDIATE EXAMPLE 1

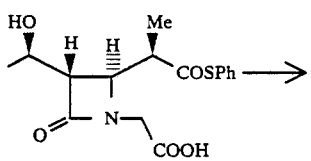

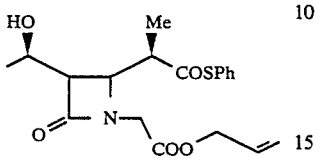

(3S,4S)-3-[(1R)-1-Hydroxyethyl]-4-[(1R)-1-phenyl-thiocarbonylethyl]-1-carboxymethyl-2-azetidinone (content, 92.8%; 13.15 g) was dissolved in allyl alcohol (14.4 ml). To the resultant mixture, chlorotrimethylsilane (10.8 ml) was added at room temperature, followed by stirring for 1.5 hours. To the reaction mixture, toluene (50 ml) was added, followed by concentration under reduced pressure. The residue was purified by silica gel column chromatography to give (3S,4S)-3-[(1R)-1-hydroxyethyl]-4-[(1R)-1-phenylthiocarbonylethyl]-1-allyloxycarboxymethyl-2-azetidinone (13.4 g; yield, 98.2%).

$IR_{max}^{neat}$ (cm$^{-1}$): 3450, 1745, 1695, 1410, 1372, 1195, 1130, 950, 745.

NMR δ(CDCl$_3$): 1.33 (3H, d, J=6.2 Hz), 1.34 (3H, d, J=6.9 Hz), 3.16 (2H, m), 3.88 (1H, AB$_d$, J=18.1 Hz), 4.17 (1H, dd, J =2.3 and 4.3 Hz), 4.23 (1H, quintet, J=6.2 Hz), 4.34 (1H, AB$_d$, J=18.1 Hz), 4.62 (2H, d, J=5.9 Hz), 5.25 (1H, d, J=10.2 Hz), 5.32 (1H, d, J=17.2 Hz), 5.88 (1H, m), 7.42 (5H).

INTERMEDIATE EXAMPLE 2

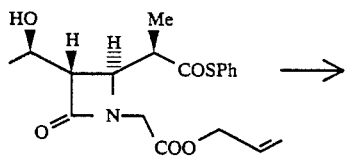

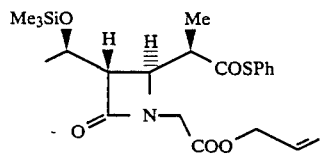

(3S,4S)-3-[(1R)-1-Hydroxyethyl]-4-[(1R)-1-phenyl-thiocarbonylethyl]-1-allyloxycarbonylmethyl-2-azetidinone (content, 90.6%; 14.7 g) was dissolved in dry toluene (60 ml), and chlorotrimethylsilane (7.8 g) and triethylamine (7.8 g) were added thereto under ice-cooling, followed by stirring at room temperature for 40 minutes. The reaction mixture was diluted with toluene (300 ml), washed with 2% sodium bicarbonate solution (300 ml) and aqueous sodium chloride (300 ml×2) and dried over magnesium sulfate to give (3S,4S)-3-[(1R)-1-trimethylsilyloxyethyl]-4-[(1R)-1-phenylthiocarbonylethyl]-1-allyloxycarbonylmethyl-2-azetidinone (16.35 g; yield, 90%).

$IR_{max}^{neat}$ (cm$^{-1}$): 1765, 1750 (sh), 1700, 1410, 1370, 1250, 1190, 980, 840, 745.

NMR δ(CDCl$_3$): 0.15 (9H, s), 1.29 (6H, d, J=6.9 Hz), 3.08 (1H, dd, J=2.3 and 7.6 Hz), 3.15 (1H, d$_Q$, J=2.3 and 6.9 Hz), 3.85 (1H, AB$_d$, dg, J=17.2 Hz), 4.1–4.2 (2H, m), 4.33 (1H, AB$_d$, J=17.2 Hz), 4.60 (2H, d, J=5.6 Hz), 5.2–5.3 (2H, m), 5.8–5.92 (1H, m), 7.41 (5H, m).

INTERMEDIATE EXAMPLE 3

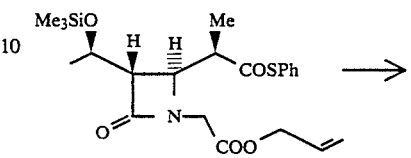

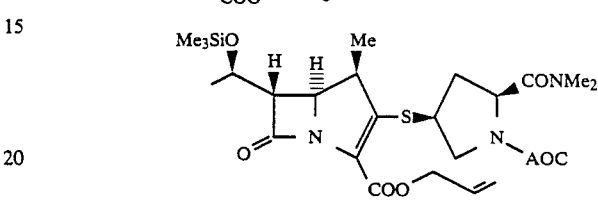

(3S,4S)-3-[(1R)-1-Trimethylsilyloxyethyl]-4-[(1R)-1-phenylthiocarbonylethyl]-1-allyloxycarbonylmethyl-2-azetidinone (content, 90%; 1.0 g) was dissolved in a dry mixture (5.5 ml) of toluene and tetrahydrofuran (4:1), and the resultant solution was dropwise added to a mixture of sodium hydride (60% oil suspension; 200 mg; 5 mM), benzyl bromide (410 mg; 2.4 mM) and trimethylsilanol (2.7 mg) in a dry mixture (8.5 ml) of toluene and tetrahydrofuran (4:1) at −15° to −10° C., followed by stirring for 2 hours. A solution of diphenyl chlorophosphate (590 mg; 2.2 mM) in toluene (1 ml) was added thereto at the same temperature, and stirring was continued for 4 hours. A solution of (2S,4S)-1-allyloxycarbonyl-2-dimethylaminocarbonyl-4-mercaptopyrrolidine (670 mg; 2.6 mM) in tetrahydrofuran (1 ml) was dropwise added thereto, 1,8-diazabicyclo[5.4.0]undec-7-ene (426 mg; 2.8 mM) was then added thereto and the resultant mixture was stirred at −15° to −10° C. overnight. To the reaction mixture, 0.1 M aqueous potassium dihydrogen phosphate (10 ml) was added, and the aqueous layer and the organic layer are separated. The aqueous layer was extracted with toluene (5 ml×2), and the toluene extract was combined with the organic layer. The resulting mixture was washed with 0.1 M phosphate buffer (pH, 7.0) and aqueous sodium chloride in order and dried over a mixture of magnesium sulfate and potassium carbonate (1:1), followed by removal of the solvent under reduced pressure. The residue was purified by silica gel column chromatography to give (4R,5S,6S,8R,2'S,4'S)-allyl-3-[4-(1-allyloxycarbonyl-2-dimethylaminocarbonylpyrrolidinyl)thio]-4-methyl-6-(1-tri-methylsilyloxyethyl)-1-azabicyclo[3.2.0]hept-2-en-7-one-2-carboxylate (0.90 g).

$IR_{max}^{neat}$(cm$^{-1}$): 1770, 1705, 1655, 1405, 1320, 1210, 1135, 980, 840.

INTERMEDIATE EXAMPLE 4

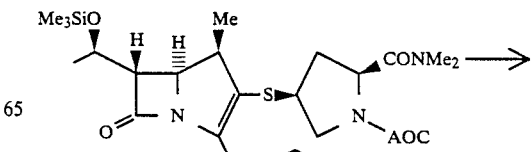

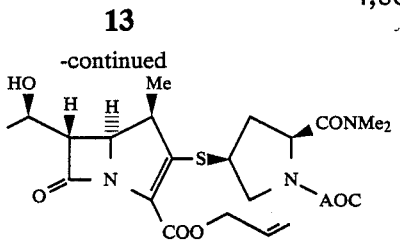

(4R,5S,6S,8R,2'S,4'S)-Allyl-3-[4-(1-allyloxycarbonyl-2-dimethylaminocarbonylpyrrolidinyl)thio]-4-methyl-6-(1-trimethylsilyloxyethyl)-1-azabicyclo[3.2.0-]hept-2-en-7-one-2-carboxylate (600 mg; 1.04 mM) was dissolved in tetrahydrofuran (6 ml), followed by addition of a citrate buffer (3 ml; pH, 3). The resultant mixture was vigorously stirred at room temperature for 1.5 hours, diluted with ethyl acetate (30 ml), washed with aqueous sodium chloride solution and dried over a mixture of magnesium sulfate and potassium carbonate (1:1). Removal of the solvent under reduced pressure gave (4R,5S,6S,8R,2'S,4'S)-allyl-3-[4-(1-allyloxycarbonyl-2-dimethylaminocarbonylpyrrolidinyl)thio]-4-methyl-6-(1-hydroxyethyl)-1-azabicyclo[3.2.0]hept-2-en-7-one-2-carboxylate.

UV$\lambda_{max}^{CH3CN}$: 317 nm.

IR$_{max}^{neat}$(cm$^{-1}$): 3420, 1770, 1705, 1645, 1550, 1405, 1320, 1278, 1205, 1175, 1135, 975, 750.

NMR δ(CDCl$_3$): 1.26 (3H), 1.36 (3H), 1.94 (1H, m), 2.67 (1H, m), 2.97 2.99, 3.06, 3.11 (total 6H, each singlet), 3.2–3.7 (4H, m), 4.25 (2H, m), 4.47–4.87 (5H, m), 5.15–5.5 (4H, m), 5.94 (2H, m).

INTERMEDIATE EXAMPLE 5

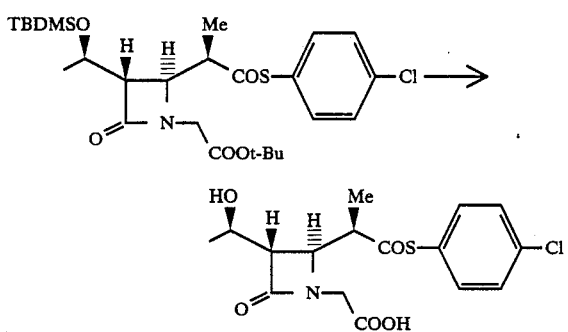

(3S,4S)-3-[(1R)-1-t-Butyldimethylsilyloxyethyl]-4-[(1R)-1-p-chlorophenylthiocarbonylethyl]-1-t-butoxycarbonylmethyl-2-azetidinone (1.0 g) was dissolved in dry methylene chloride (10 ml), and anisole (497 mg) and boron trifluoride-diethyl ether complex (1.04 g) were added thereto, followed by stirring at 38° to 42° C. for 3 hours. The organic layer was shaken with water and aqueous sodium bicarbonate. The aqueous layer was separated, adjusted to pH 1 with concentrated hydrochloric acid and extracted with ethyl acetate. The extract was dried over anhydrous sodium sulfate and concentrated under reduced pressure. Ethyl acetate (1 ml) was added to the residue, and the resultant mixture was warmed at 50° C. After dropwise addition of toluene (5 ml), the resultant mixture was stirred for 30 minutes and allowed to cool to room temperature. The precipitated crystals were collected by filtration and dried to give (3S,4S)-3-[(1R)-1-hydroxyethyl]-4-[(1R)-1-p-chlorophenylthiocarbonylethyl]-1-(1-carboxymethyl)-2-azetidinone. m.p., 81°–83° C.

IR$_{max}^{CHCl3}$(cm$^{-1}$): 3400 (br), 1748, 1700, 1475, 1383, 1190, 1090.

NMR δ (CDCl$_3$): 1.29 (3H, d), 1.31 (3H, d), 3.16 (2H, m), 4.08 (2H, ABq, J=18.1 Hz), 4.22 (1H, dd, J=2.3 and 4.3 Hz), 4.27 (1H, m), 7.35 (4H, ABq, J=8.6 Hz).

INTERMEDIATE EXAMPLE 6

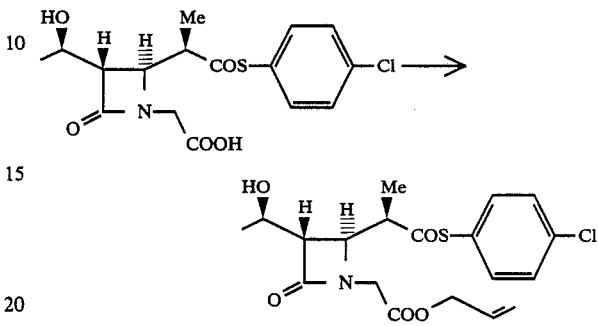

(3S,4S)-3-[(1R)-1-Hydroxyethyl]-4-[(1R)-1-p-chlorophenylthiocarbonylethyl]-1-(1-carboxymethyl)-2-azetidinone (371 mg) was dissolved in allyl alcohol (0.4 ml), trimethylchlorosilane (0.3 ml) was added thereto, and the resultant mixture was stirred at room temperature for 1 hour. After removal of the solvent, the residue was purified by silica gel column chromatography to give (3S,4S)-3-[(1R)-1-hydroxyethyl]-4-[(1R)-1-p-chlorophenylthiocarbonylethyl]-1-(1-allyloxycarbonylmethyl)-2-azetidone.

IR$_{max}^{neat}$(cm$^{-1}$): 3430, 1763 (sh), 1740, 1698, 1477, 1383, 1190, 950, 723.

NMR δ (CDCl$_3$): 1.32 (3H, d, J=6.6 Hz), 1.33 (3H, d, J=6.9 Hz), 2.36 (1H, brs), 3.15 (2H, m), 4.10 (2H, AB$_q$, J=18.1 Hz), 4.17 (1H, dd, J=2.3 and 4.3 Hz), 4.22 (1H, m), 4.62 (2H, d, J=5.9 Hz), 5.28 (2H, m), 5.87 (1H, m), 7.35 (4H, AB$_q$, J=8.6 Hz).

INTERMEDIATE EXAMPLE 7

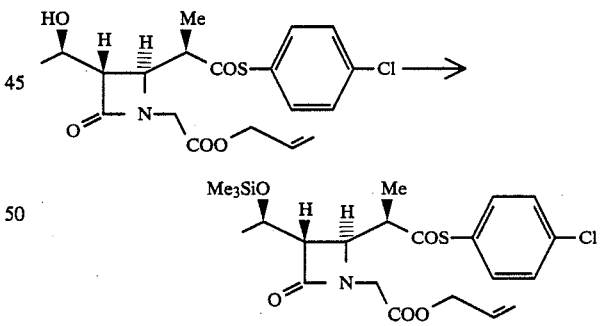

(3S,4S)-3-[(1R)-1-Hydroxyethyl]-4-[(1R)-1-p-chlorophenylthiocarbonylethyl]-1-(1-allyloxycarbonylmethyl)-2-azetidinone (305 mg) was dissolved in dry toluene (1.5 ml), trimethylchlorosilane (145 mg) and triethylamine (150 mg) were added thereto, and the resultant mixture was stirred at room temperature for 1 hour. The organic layer was washed with 2% aqueous sodium bicarbonate and a saturated sodium chloride solution in order, dried over anhydrous sodium sulfate and concentrated under reduced pressure to give (3S,4S)-3-[(1R)-1-trimethylsilyloxyethyl]-4-[(1R)-p-chlorophenylthiocarbonylethyl]-1-(1-allyloxycarbonylmethyl)-2-azetidinone.

IR$_{max}^{neat}$(cm$^{-1}$): 1762, 1740, 1702, 1475, 1245, 1086, 976, 837.

NMR δ (CDCl₃): 0.14 (9H, s), 1.30 (3H, d, J=6.9 Hz), 1.30 (3H, d, J=6.6 Hz), 3.07 (1H, m), 3.14 (1H, d$_q$, J=3.3 and 6.9 Hz), 4.08 (2H, AB$_q$, J=17.8 Hz), 4.10 (1H, m), 4.16 (1H, m), 4.60 (2H, dt, J=1.3 and 5.6 Hz), 5.27 (2H, m), 5.88 (1H, m), 7.35 (4H, AB$_q$, J=8.6 Hz).

INTERMEDIATE EXAMPLE 8

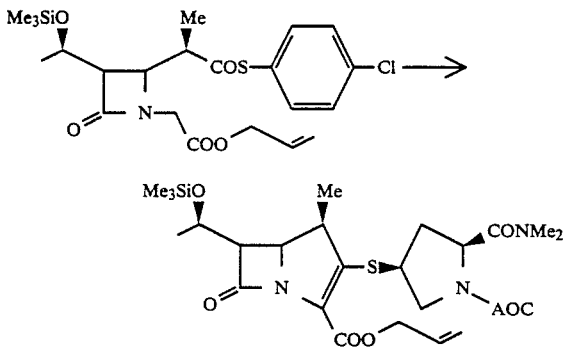

(3S,4S)-3-[(1R)-1-Trimethylsilyloxyethyl]-4-[(1R)-1-phenylthiocarbonylethyl]-1-allyloxycarbonylmethyl-2-azetidinone (308 mg) was dissolved in a dry mixture (2 ml) of toluene and tetrahydrofuran (4:1), and the resultant solution was dropwise added to a mixture of sodium hydride (60% oil suspension; 89.2 mg; 2.23 mM), allyl bromide (77.4 mg; 0.64 mM) and trimethylsilanol (0.864 mg) in a dry mixture (2.5 ml) of toluene and tetrahydrofuran (4:1) at −15° C., followed by stirring at −15° to −10° C. for 2 hours. A solution of diphenyl chlorophosphate (207 mg; 0.77 mM) in toluene (0.5 ml) was dropwise added thereto at the same temperature, and stirring was continued for 2 hours. A solution of (2S, 4S)-1-allyloxycarbonyl-2-dimethylamino-carbonyl-4-mercaptopyrrolidine (165 mg; 0.64 mM) in tetrahydrofuran (1 ml) was dropwise added thereto, and the resultant mixture was stirred at −5° to 0° C. for 1 hour. To the reaction mixture, 0.1 M aqueous potassium dihydrogen phosphate (5 ml) was added, and the aqueous layer was separated and extracted with ethyl acetate (5 ml). The extract was combined with the organic layer, washed with aqueous sodium chloride, dried over a mixture of magnesium sulfate and potassium carbonate (1:1) and concentrated under reduced pressure. The residue was purified by silica gel column chromatography to give (4R,5S,6S,8R,2'S,4'S)-allyl-3-[4-(1-allyloxycarbonyl-2-dimethylaminocarbonylpyrrolidinyl)thio]-4-methyl-6-(1-trimethylsilyloxyethyl)-1-azabicyclo[3.2.0]hept-2-en-7-one-2-carboxylate. The IR spectrum of this product was identical to that of the product obtained in Intermediate Example 3.

INTERMEDIATE EXAMPLE 9

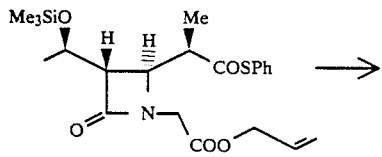

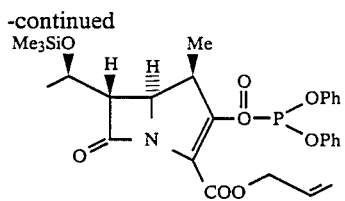

(3S,4S)-3-[(1R)-1-Trimethylsilyloxyethyl]-4-[(1R)-1-phenylthiocarbonylethyl]-1-allyloxycarbonylmethyl-2-azetidinone (content, 90%; 15 g) was dissolved in a dry mixture (65 ml) of toluene and tetrahydrofuran (4:1), and the resultant solution was dropwise added to a suspension of sodium hydride (60% oil suspension; 4.2 g; 105 mM), allyl bromide (4.0 g; 33 mM) and trimethylsilanol (28 mg) in a dry mixture (115 ml) of toluene and tetrahydrofuran (4:1) at −15° to −10° C., followed by stirring for 3 hours. A solution of diphenyl chlorophosphate (9.67 g; 36 mM) in a dry mixture of toluene and tetrahydrofuran (4:1) (15 ml) was added thereto at the same temperature, and stirring was continued for 4 hours. Few drops of 0.1 M phosphate buffer (pH, 7.0) were added thereto, and the reaction was interrupted. 0.1 M Phosphate buffer (pH, 7.0; 150 ml) was added thereto, and the reaction mixture was extracted with ethyl acetate (150 ml). The aqueous layer was again extracted with ethyl acetate (100 ml). The extract was combined with the organic layer, washed with saturated sodium chloride solution and dried over a mixture of magnesium sulfate and potassium carbonate (1:1), followed by removal of the solvent under reduced pressure. The residue was subjected to silica gel column chromatography using a mixture of toluene and ethyl acetate (95:5–90:10) as an eluent, and the eluted fractions were concentrated to give (4R,5R,6S,8R)-allyl-3-(diphenylphosphoryloxy)-4-methyl-6-(1-trimethylsilyloxyethyl)-1-azabicyclo[3.2.0]hept-2-en-7-one-2-carboxylate.

IR$_{max}^{neat}$(cm$^{-1}$): 1780, 1725, 1630, 1588, 1483, 1285, 1250, 1182, 955.

NMR δ (CDCl₃): 0.11 (9H, s), 1.19 (3H, d, J=7.3 Hz), 1.25 (3H, d, J=6.3 Hz), 3.24 (1H, dd, J=3.0 and 6.6 Hz), 3.46 (1H, m), 4.11 (1H, dd, J=3.0 and 10.6 Hz), 4.18 (1H, m), 4.66 (2H, d, J=5.61 Hz), 5.20 (1H, d, J=10.6 Hz), 5.37 (1H, d, J=17.2 Hz), 5.86 (1H, m), 7.21–7.41 (10H, m).

INTERMEDIATE EXAMPLE 10

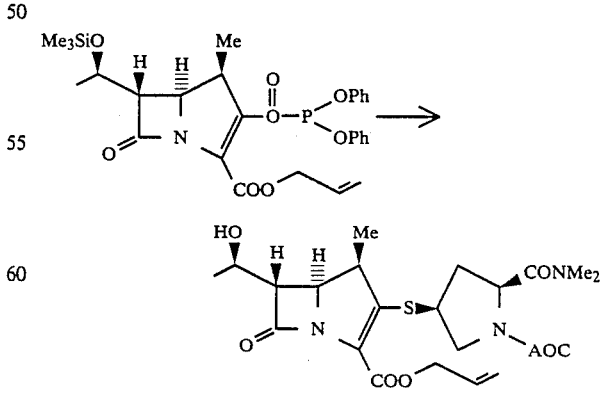

(4R,5R,6S,8R)-Allyl-3-(diphenylphosphoryloxy)-4-methyl-6-(1-trimethylsilyloxyethyl)-1-azabicyclo[3.2.0]hept-2-en-7-one-2-carboxylate (290 mg) was dissolved in dry acetonitrile (1.5 ml), and (2S,4S)-1-allyloxycarbonyl-2-dimethylaminocarbonyl-4-mercaptopyrrolidine (142 mg) was added thereto, followed by cooling to −15° C. A solution of diisopropylethylamine (77.5 mg) in dry acetonitrile (about 0.2 ml) was dropwise added thereto, and the resultant mixture was stirred at −15° to −10° C. for 5 hours. To the reaction mixture, 0.1 M aqueous potassium dihydrogen phosphate (10 ml) and ethyl acetate (10 ml) were added, and the aqueous layer and the organic layer were separated. The organic layer was washed with 0.1 M aqueous potassium dihydrogen phosphate (10 ml). After confirming the pH of the aqueous layer being 4 to 5, the organic layer was stirred at room temperature for 5 to 15 hours. Elimination of the trimethylsilyl group was confirmed by thin layer chromatography using a mixture of benzene and acetic acid (1:1). The resultant organic solution was washed with a saturated aqueous sodium chloride solution, dried over a mixture of magnesium sulfate and potassium carbonate (1:1) and concentrated under reduced pressure. The residue was purified by silica gel column chromatography to give (4R,5S,6S,8R,2'S,4'S)-allyl-3-[4-(1-allyloxycarbonyl-2-dimethylaminocarbonyl)pyrrolidinylthio]-4-methyl-6-(1-hydroxyethyl)-1-azabicyclo[3.2.0]hept-2-en-7-one-2-carboxylate. This product was identical with the one obtained in Intermediate Example 4 with regard to UV, IR and NMR data.

INTERMEDIATE EXAMPLE 11

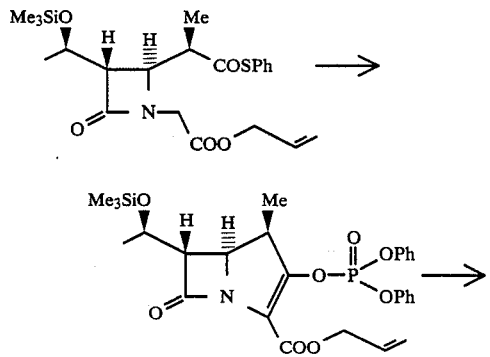

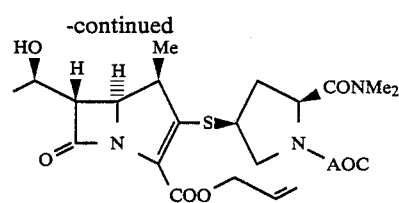

Crude (4R,5R,6S,8R)-allyl-3-(diphenylphosphoryloxy)-4-methyl-6-(1-trimethylsilyloxyethyl)-1-azabicyclo[3.2.0]hept-2-en-7-one-2-carboxylate obtained in Reference Example 9 was subjected to the same treatment as in Reference Example 10 to give (4R,5S,6S,8R,2'S,4'S)-allyl-3-[4-(1-allyloxycarbonyl-2-dimethylaminocarbonyl)pyrrolidinylthio]-4-methyl-6-(1-hydroxyethyl)-1-azabicyclo[3.2.0]hept-2-en-7-one-2-carboxylate.

What is claimed is:

1. Crystalline (4R, 5S, 6S, 8R, 2'S, 4'S)-3-[4-(2-Dimethylaminocarbonyl)pyrrolidinylthio]-4-methyl-6-(1-hydroxyethyl)- 1-azabicyclo [3.2.0]hept-2-en-7-one-2-carboxylic acid trihydrate of the formula:

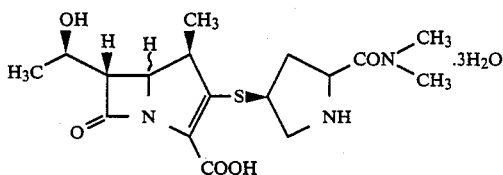

2. A pharmaceutical composition for being dissolved in a physiologically acceptable aqueous medium and injected into a human body, which comprises as an active ingredient crystalline (4R, 5S, 6S, 8R, 2'S, 4'S)-3-[4-2-dimethylaminocarbonyl)pyrrolidinylthio]-4-methyl-6-(1-hydroxyethyl)-1-azabicyclo[3.2.0]hept-2-en-7-one-2-carboxylic acid trihydrate of the formula:

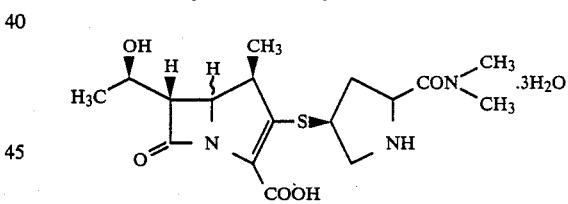

and a non-toxic carbonate.

3. The composition according to claim 2, wherein the non-toxic carbonate is sodium carbonate.

4. The composition according to claim 2, wherein the non-toxic carbonate is sodium bicarbonate.

* * * * *

UNITED STATES PATENT AND TRADEMARK OFFICE
CERTIFICATE OF CORRECTION

PATENT NO. : 4,888,344

DATED : December 19, 1989

INVENTOR(S) : Makoto Sunagawa, Yutaka Isobe, Yutaka Takeuchi, Haruki Matsamura, Yukio Ozaki and Tetsuo Noguchi It is certified that error appears in the above-indentified patent and that said Letters Patent is hereby corrected as shown below:

TITLE PAGE:

In the Abstract of the Disclosure, please delete the following Formula

"
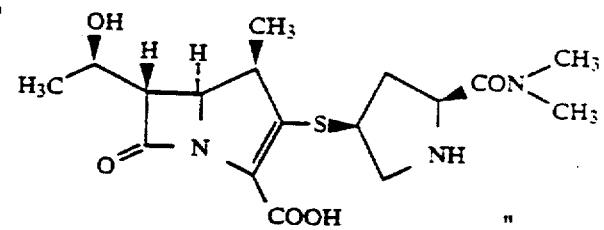
"

and replace with the following Formula

—
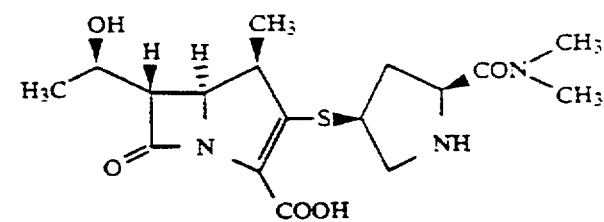
—

Column 1, Line 15, change Formula

"
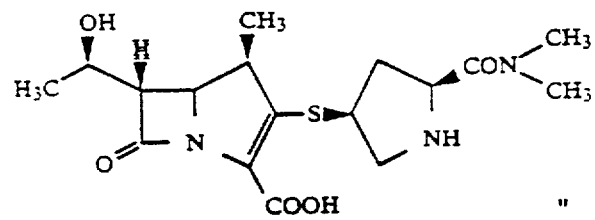
"

UNITED STATES PATENT AND TRADEMARK OFFICE
CERTIFICATE OF CORRECTION

PATENT NO. : 4,888,344

DATED : December 19, 1989

INVENTOR(S) : Makoto Sunagawa, Yutaka Isobe, Yutaka Takeuchi, Haruki Matsamura, Yukio Ozaki and Tetsuo Noguchi It is certified that error appears in the above-identified patent and that said Letters Patent is hereby corrected as shown below:

to —

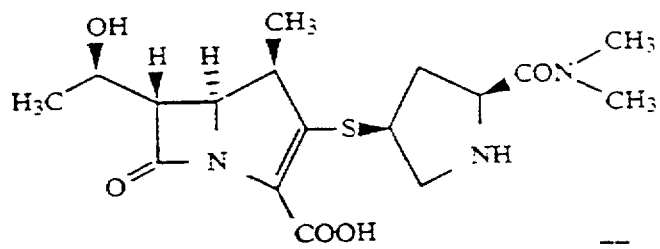

—

Column 18
Please delete the Formula in Claim 1
"
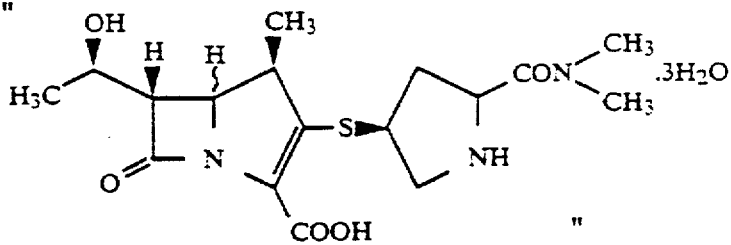
"

and replace with the following Formula
—
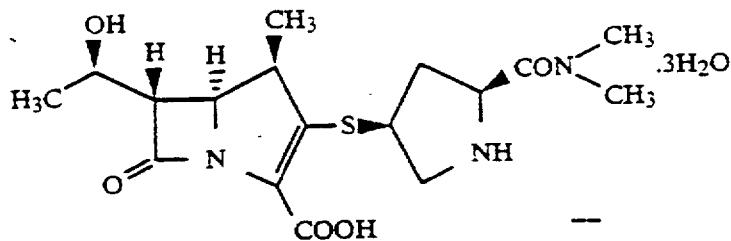
—

UNITED STATES PATENT AND TRADEMARK OFFICE
CERTIFICATE OF CORRECTION

PATENT NO. : 4,888,344

DATED : December 19, 1989

INVENTOR(S) : Makoto Sunagawa, Yutaka Isobe, Yutaka Takeuchi, Haruki Matsamura, Yukio Ozaki and Tetsuo Noguchi Page 3 of 4

It is certified that error appears in the above-indentified patent and that said Letters Patent is hereby corrected as shown below:

Column 18

Line 5, change " 4-2-dimethylaminocarbonyl)pyrrolidinylthio "

to -- 4-(2-dimethylaminocarbonyl)pyrrolidinylthio --

Please delete the Formula " in claim 2

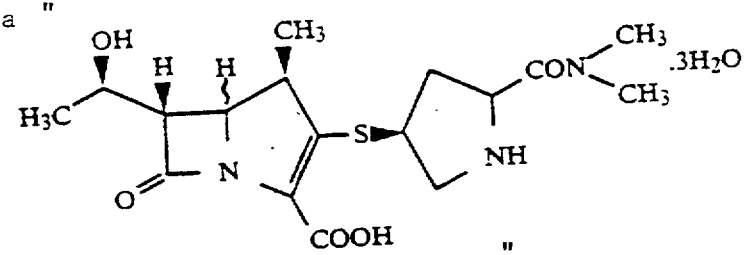

"

UNITED STATES PATENT AND TRADEMARK OFFICE
CERTIFICATE OF CORRECTION

PATENT NO. : 4,888,344

DATED : December 19, 1989

INVENTOR(S) : Makoto Sunagawa, Yutaka Isobe, Yutaka Takeuchi, Haruki Matsamura, Yukio Ozaki and Tetsuo Noguchi It is certified that error appears in the above-indentified patent and that said Letters Patent is hereby corrected as shown below:

and replace with the following Formula

--

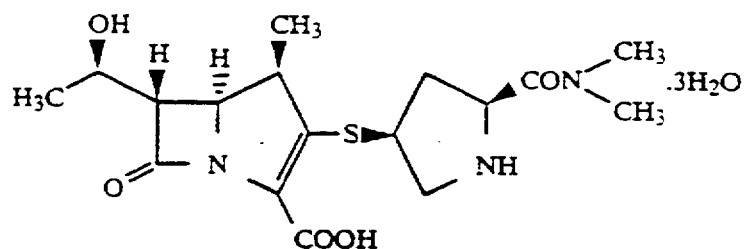

--

Signed and Sealed this

Twenty-third Day of August, 1994

Attest:

BRUCE LEHMAN

Attesting Officer

Commissioner of Patents and Trademarks